United States Patent [19]

Bruhn

[11] Patent Number: 4,878,384

[45] Date of Patent: Nov. 7, 1989

[54] DEVICE FOR EVALUATING AND MEASURING HUMAN SENSORY PERCEPTION

[76] Inventor: Theodor Bruhn, Calenberger Strasse 15, D-3017, Pattensen, Fed. Rep. of Germany

[21] Appl. No.: 147,966

[22] Filed: Jan. 25, 1988

[30] Foreign Application Priority Data

Jan. 30, 1987 [DE] Fed. Rep. of Germany ....... 3702808

[51] Int. Cl.[4] ........................... A61B 5/22; G01D 1/00
[52] U.S. Cl. .................................. 73/379; 73/862.53; 273/1 GE
[58] Field of Search ..................... 73/862.53, 770, 379; 273/1 GE, 1 GC; 128/774, 744, 26

[56] References Cited

U.S. PATENT DOCUMENTS 3,670,573  6/1972  Kroemer ............................... 73/379
4,501,148  2/1985  Nicholas et al. ............. 73/862.53 X
4,534,557  8/1985  Bigelow et al. .................. 273/1 GE
4,613,130  9/1986  Watson .............................. 128/26 X

FOREIGN PATENT DOCUMENTS 83568      7/1983  European Pat. Off. .
2912981   10/1980  Fed. Rep. of Germany .
3518489   12/1986  Fed. Rep. of Germany .

OTHER PUBLICATIONS

Johnson, Arthur T., "Analog Sample/Hold Circuit For Physiological Signal Monitoring", *IEEE Transactions on Biomedical Engineering*, Sep. 1975, pp. 420–423.

*Primary Examiner*—Charles A. Ruehl
*Attorney, Agent, or Firm*—Beveridge, DeGrandi & Weilacher

[57] ABSTRACT

A device for evaluating and measuring human sensory perceptions by measuring muscle force applied against a finger button and displaying a maximum muscle force. To obtain an objective measurement, the device according to the invention includes a delay circuit and a display unit. The delay circuit is actuated at the start of a muscle force measurement by a maximum muscle force detector and then the display unit is actuated after a delay of approximately 3 seconds caused by the delay circuit. Preferably, an acoustic signal is provided after the 3 second delay along with a first visual display by the display unit.

7 Claims, 1 Drawing Sheet

DEVICE FOR EVALUATING AND MEASURING HUMAN SENSORY PERCEPTION

BACKGROUND OF THE INVENTION

The invention relates to a device for evaluating and measuring human sensory perception. More particularly, the present invention relates to a human sensory perception evaluating and measuring device having means for detecting muscle force including a finger button and display means for displaying the muscle force detected by the detecting means.

Devices of this type are based on the observation that the muscles of the human body produce less force when a certain stimulus occurs, e.g., due to the perception of colors, forms, noises, odors, taste and touch as well as due to thoughts, memories and the like. Comparison of the muscle forces produced before and after the sensory perception enables determination of positive or negative personal reactions.

Pressure measurements are made before and after, or during perception of the sensory stimulus/stimuli. The results of the measurements are then compared. If the second value is less than the first value, then the tested influence usually can be regarded as negative, and if the second value exceeds the first value, a positive influence is assumed.

The level of the measured values can be important; however, normally, the difference of the values is the only significant factor. Nevertheless, objective measurments have been difficult to achieve with prior art devices. The influencing time and the display devices play a part in this. It is also significant whether the applied force is constant on the finger button over the entire influencing time or whether it varies considerably. These problems are particularly significant in pocket-size devices, for spatial reasons alone.

SUMMARY OF THE INVENTION

The present invention is directed to improving the above-mentioned devices to provide the most objective measurements possible. The user is forced to follow certain procedures in order to obtain an objective measurement.

The invention achieves this objective as follows. The device according to the present invention includes a timing or delay element and a display means for presenting a display to the subject. The timing or delay element is actuated at the beginning of the pressure or muscle force measurement while the display means is actuated after a delay, preferably after a delay of several seconds, by the timing or delay element. Further, the measurement of the applied muscle force is a maximum value measurement. It is also preferable that the device be implemented such that a measured result will not be indicated until the display means is actuated.

The invention is based upon the understanding that the human subject must pay attention to the finger button for a certain time, herein referred to as the influencing time. For this reason, the timing or delay element is actuated at the start of pressure on the finger button. The display means is not activated until after the elapse of a predetermined time. An acoustic signal or a certain display then is provided. As is also apparent, it is possible to simultaneously provide both an acoustic and a visual signal. The subject or user of the device is thus informed of the desired influencing time on the finger button. In addition, it is important that only a maximum value be displayed by the display means and not, for example, an average value. Thus, maximum values are compared when the comparison is to be carried out.

It is advantageous that the measured results not be displayed until the provision of the optical and/or acoustic signal and not immediately or in a variable manner during the course of the measurement. This is based on the premise that the user will be inclined to depress the finger button until a measured result is obtained at the display. This provides for a certain measuring time wherein the subject will not operate the finger button in an intermittent or "jerky" manner.

BRIEF DESCRIPTION OF THE DRAWINGS

The details and features of the invention are explained below with reference to the drawings which show a preferred embodiment of the invention. In the drawings.

DETAILED DESCRIPTION OF THE PREFERRED EMBODIMENT

A preferred human sensory perception evaluating and measuring device A according to the present invention is provided in a parallelepiped housing 1. Generally, the housing 1 contains a pressure responsive element, an electronic circuit, a display and, optionally, a current source.

Figure 2:
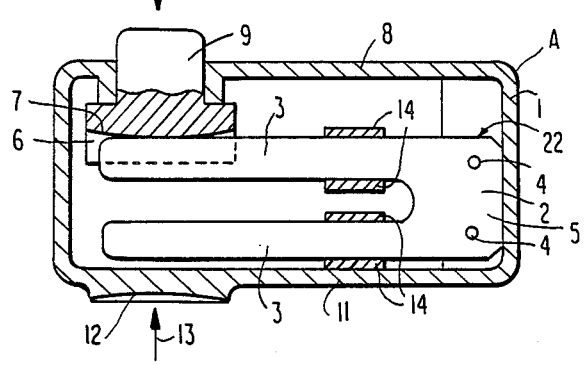
FIG. 2 is a sectional view along line II—II of FIG. 1.

A pressure responsive element, generally identified by reference numeral 22, comprises a U-shaped member 2 constructed from aluminum to have shanks 3 connected by a crosspiece 5 which has holes therein for receiving fastening means. One of the shanks 3, namely the upper shank in FIG. 2, is received in a slot 6 in a lower, widened portion 7 of a push button 9. Generally, the lower widened portion 7 of the push button 9 is convexly shaped. The push button 9 is received and guided in an opening in the top 8 of the housing and extends upwardly to project from top 8. The other or lower shank 3 rests on the bottom portion 11 of housing 1. A concave portion 12 is provided on the outside of the bottom portion 11 and is configured to receive the fingers of the hand of a human subject. When a force by two fingers of one hand is exerted in the direction of arrows 13, the shanks 3 are urged towards one another. In the absence of hand pressure, the shanks 3 are separated from one another.

Figure 3:
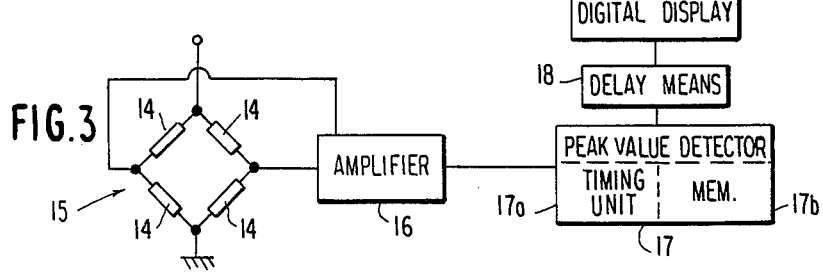
FIG. 3 is a diagram in partial schematic form of an electronic circuit used in the device of FIGS. 1 and 2.

For determination of the force exerted by the fingers of a subject, the shanks 3 are provided with wire strain gauges 14 which in turn are components of an electrical bridge 15 shown in FIG. 3. The bridge equilibrium value, which varies with the applied finger force, is received by amplifier 16, amplified, and supplied to a peak value detector 17.

Figure 1:
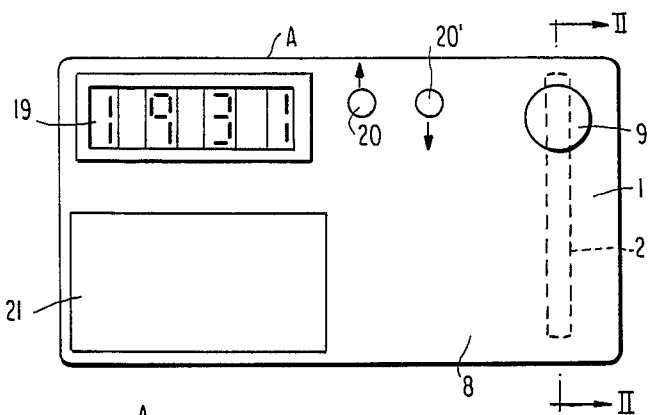
FIG. 1 is a downwardly looking view of a device for measuring and evaluating human sensory perceptions according to the present invention.

The peak value detector 17, which comprises an internal timing unit 17a, is connected to a digital display 19, shown in FIG. 1 as located in a window of the housing 1, by a delay means 18. Further, the peak value detector 17 is provided with an internal memory 17b for storing measured values.

Figure 4:
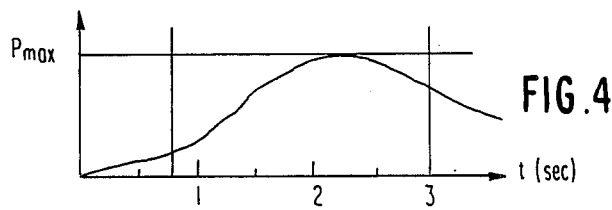
FIG. 4 is a pressure versus time diagram useful in understanding the operation of the circuit of FIG. 3.

In the diagram of FIG. 4, P designates the force exerted by the human subject's finger or fingers against the push button 9. The t axis gives the duration, in seconds, of the applied force.

When the finger button 9 is first pressed, the measuring unit does not react due to peak value detector 17. Electrical signals, which do not exceed a certain predetermined threshold value, do not produce a response in the peak value detector 17 until they reach the threshold value. Thereafter, the force detected over the time t is registered (FIG. 4). The peak value detector 17 provides a signal indicative of the maximum force or pressure value, P max, to digital display 19. Delay means 18, however, delays the signal from peak value detector 17 for 3 seconds such that only if the finger force is present for 3 seconds will a maximum pressure be displayed at the display 18. The delay means 18 does not pass the display signal from the peak value detector 17 until elapse of that time. Then, the value P max of the preceding measurement period is caused to be displayed at the display 19 for a period of 12 seconds by the timing unit 17a of the peak value detector 17 and its memory 17b. During this display period, no other measurements are registered or displayed. After 12 seconds, the display of digital display 19 is terminated. A follow-up or comparison measurement, after the sensory perception for example, is then performed to determine a positive or negative personal reaction by the measurement subject after termination of the 12 second display. It is performed in accordance with the above-described procedure, namely, that 3 seconds must first elapse before a display is provided. Likewise, only a display of the maximum value is provided and only those values which exceed a negligible threshold value are considered.

Figure 5:
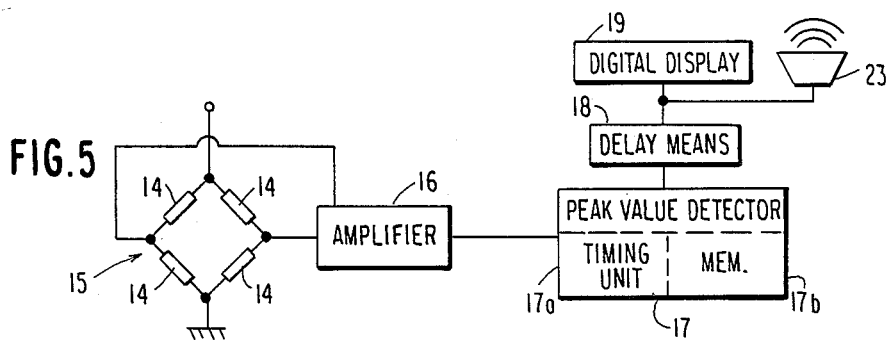
FIG. 5 is a diagram, similar to FIG. 3, of an electronic circuit including an acoustic signal providing means according to an alternative embodiment of the present invention.

As described above, the display 19 provides a display for the user after 3 seconds. The display to the user could be provided even earlier. However, a correction of the result may be required during the course of measuring in the latter case to determine the maximum value. Moreover, the passage of a 3-second period would be indicated by a special signal, preferably an acoustic signal generated by an acoustic signal generating means 23, shown in FIG. 5.

On the other hand, a display having a duration of 12 seconds is provided after the comparison measurement. Now the comparison between the two values P max may be performed either directly by a person or by an electronic instrument adapted to compare both values and display their difference either in level or by yes-no function.

It is important that the subject be prevented from determining the measurement results for a certain time, which time is 3 seconds in the preferred embodiment, so that every subject will be inclined to maintain pressure on the button until he is certain of his result. He can not determine his result until an acoustic signal is provided and/or a visual display is presented, whereupon the result is visually presented for a certain time, 12 seconds according to the embodiment, due to delay means 18. Another measurement is impossible during this time period and any pressure on the finger button would be ineffective.

According to the preferred embodiment, the two measurements can be electronically evaluated. A significant difference is indicated by the two light-emitting diode displays 20 and 20'. Diode display 20 indicates that the second measurement was greater and better and thus that there was a positive evaluation. On the other hand, if diode 20' is energized, a negative reaction by the subject is indicated.

The above-described electronic components including the bridge 15, the amplifier 16, the peak value detector 17 and the timing unit 17a and the memory 17b, the delay means 18, the display 19 and the acoustic signal generating means 23 are conventional.

Reference character 21 indicates a compartment for a battery for providing electrical energy to the electronic components of the device. Thus, the device according to the present invention can be constructed to have reduced size so that it can be carried as a pocket device.

What is claimed is:
1. Device for evaluating and measuring human sensory perceptions comprising:
   a finger button;
   signal generating means for generating a muscle force signal indicative of a maximum muscle force applied to the finger button;
   a display means responsive to the muscle force signal for displaying the maximum muscle force;
   a time measuring device responsive to muscle force applied to the finger button for commencing a time measuring operation; and
   delay means for delaying display of the maximum muscle force by the display means for a predetermined delay period whereafter the display means displays the maximum muscle force for a time measured by the measuring device.
2. Device according to claim 1, further comprising means for providing an acoustic signal during display of the muscle force by the display means.
3. Device according to claim 1, wherein the delay is about 3 seconds.
4. Device according to claim 1, wherein the time measuring device commences time measuring only after a threshold muscle force value has been applied to the finger button.
5. Device according to claim 1, wherein the display by the display means is provided for approximately 12 seconds.
6. Device according to claim 1, wherein the duration of the display means is substantially longer than the delay period of the delay means.
7. Device according to claim 1, wherein muscle force applied to the finger button during display of the maximum muscle force by the display means is ineffective.

* * * * *